United States Patent
Hopkins, Jr. et al.

[11] Patent Number: 6,130,753
[45] Date of Patent: Oct. 10, 2000

[54] LASER OPTICAL DENSITY MEASUREMENT SYSTEM

[75] Inventors: Richard A. Hopkins, Jr., Converse; Benjamin A. Rockwell, San Antonio, both of Tex.

[73] Assignee: The United States of America as represented by the Secretary of the Air Force, Washington, D.C.

[21] Appl. No.: 09/241,192

[22] Filed: Feb. 1, 1999

[51] Int. Cl.[7] .................................................. G01N 21/00
[52] U.S. Cl. ............................................................ 356/435
[58] Field of Search .................................. 356/433, 434, 356/435, 243

[56] References Cited

U.S. PATENT DOCUMENTS

| | | | |
|---|---|---|---|
| 3,923,397 | 12/1975 | Shuck | 356/39 |
| 4,068,956 | 1/1978 | Taboada | 356/434 |
| 5,032,024 | 7/1991 | Cope | 356/41 |

*Primary Examiner*—Robert H. Kim
*Assistant Examiner*—Layla Lauchman
*Attorney, Agent, or Firm*—Tony Y. Cole; Bobby D. Scearce; Thomas L. Kundert

[57] ABSTRACT

An apparatus for measuring optical density of highly absorptive materials in which a beam splitter divides light from a laser source into a reference beam, which is directed to a reference detector, and a sample beam, which is reflected off a diffusing plate, through a light limiting aperture, and to a sample. The emanations from the sample are directed to a sample detector. An instrumentation amplifier compares the intensities of the two detectors. The aperture and reference detector are positioned so that the measured intensities are equal, and the optical density of the sample is calculated.

5 Claims, 1 Drawing Sheet

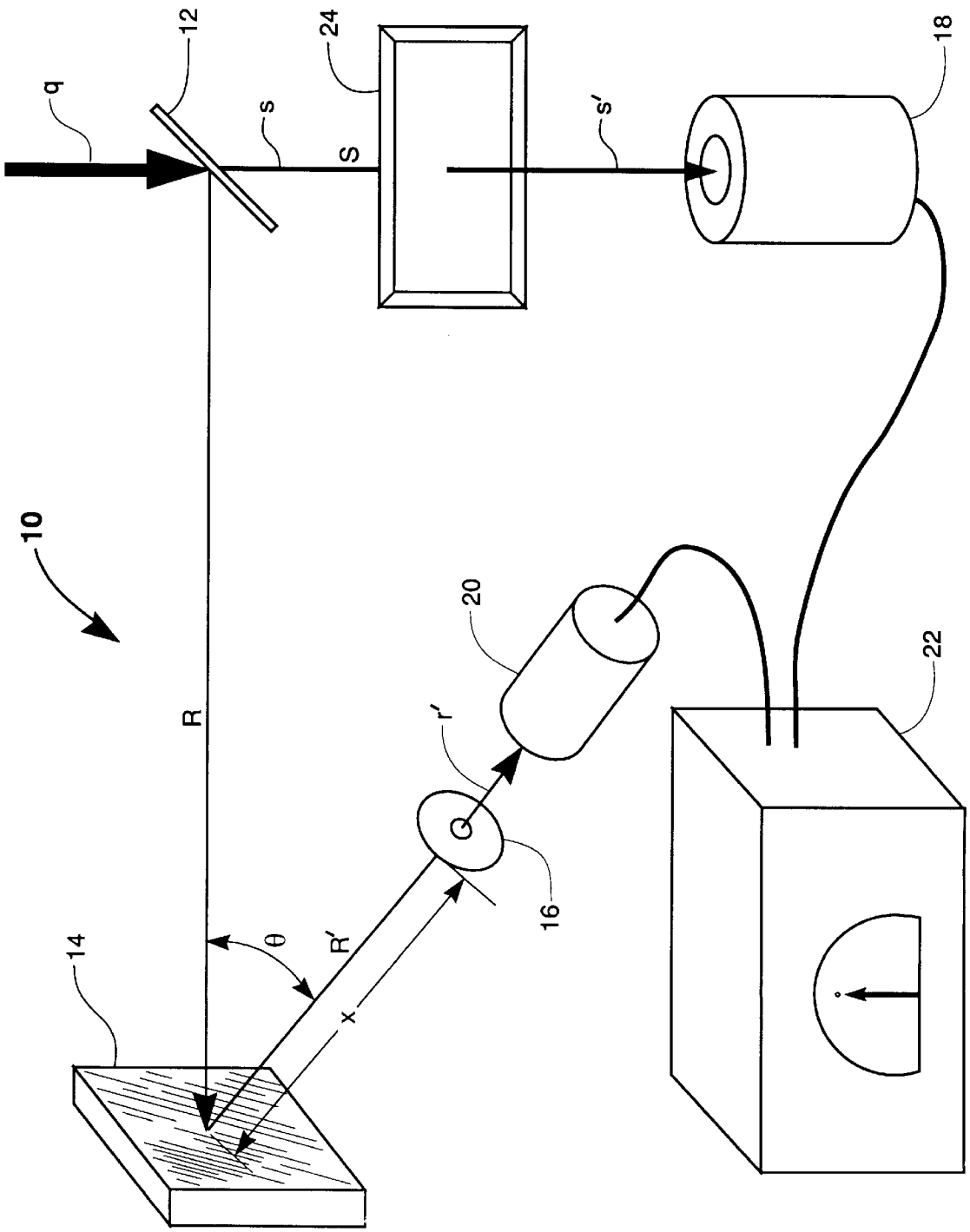

LASER OPTICAL DENSITY MEASUREMENT SYSTEM

RIGHTS OF THE GOVERNMENT

The invention described herein may be manufactured and used by or for the Government of the United States for all governmental purposes without the payment of any royalty.

BACKGROUND OF THE INVENTION

The present invention relates generally to systems for measuring optical density and, more particularly, to a novel field usable densitometer for measuring very optically dense materials, such as laser eye protection and optical filters used to protect light-sensitive detectors and instruments.

The use of lasers has become widespread, especially in military equipment on the battlefield. Laser damage can be intentionally inflicted, as from offensively used lasers, or inadvertently, as from lasers used for range finders, targeting, and measuring devices. In military situations, the eyes of personnel and the detectors of sensitive optical instruments need protection from damaging laser radiation. In non-military situations, it is necessary to provide protection from laser radiation to individuals working near or with laser containing equipment. Optical filters are used to block high intensity pulsed or continuous wave laser beams in the visible, near infrared and ultraviolet portions of the spectrum, to prevent eye damage and damage to detectors in the path of the laser beam.

Filter protection is described in terms of optical density, which logarithmically relates transmitted energy to incident energy. If a filter has an optical density of one, it absorbs 90% of the incident energy and transmits 10%; with a density of 2, it would transmit $1/100$ of the incident energy. An optical density of 5 means the filter has reduced the power of the laser beam to $1/100,000$ of its original power. To be effective, protective filters must have a high optical density at the selected wavelength. Sun glasses normally have an optical density of less than 1 across the entire visible spectrum, but for laser protection, optical densities as high as 10 are desirable at very specific wavelengths.

For purposes of measuring optical densities, it is well known to employ an instrument known as a double beam spectrophotometer. A double-beam spectrophotometer typically includes a light source, a monochromator, a beam splitter, a sample detector, and a reference detector. These components, together with a standard power supply, normally occupy a volume of at least one cubic foot. The light source provides a beam of light, which is split by the beam splitter into two beams. One of the light beams is directed through a sample before or after passing through the monochromator to the sample detector. The monochromator divides a polychromatic beam into a nearly monochromatic beam. The other beam passes unimpeded to the reference detector. The intensities of the light beams measured by the detectors are compared, the ratio being indicative of the optical density of the sample. Typically, the instrument is calibrated against a sample of known optical density and, thereafter, unknown samples are examined.

There are various possibilities for the choice of the main components of spectrophotometers. The light source usually comprises a continuous-emission lamp, such as halogen, deuterium, tungsten or xenon. Prism or grating dispersion devices are used for the monochromator. The detectors are generally photomultipliers, phototubes or silicon photodiodes. The beam splitter is typically a flat quartz plate or a partially reflecting mirror. The various kinds of available components and the various possible structures can be combined in numerous ways to construct a double beam spectrophotometer.

A low optical density, up to about 4, can be measured directly on a double beam spectrophotometer for wavelengths within its operating range. However, to ensure eye safety, many commercial laser eye protectors have very high optical densities at some laser wavelengths. As indicated previously, optical densities in the range of 8 to 10 are not uncommon for protective optical filters. Such high attenuations are beyond the capabilities of the double beam spectrophotometer to measure. Instead, inaccurate extrapolations of spectrophotometer transmission measurements must be made.

As indicated previously, spectrophotometric measurements give the optical density of the filter or other material to a narrow-band, low-power, continuous wave light source, such as halogen, deuterium, tungsten or xenon. The surest way to confirm the protection capability of a laser-protective filter, however, is to expose the filter directly to the laser which is desired to be protected against. Moreover, the advantageous characteristics of laser light, in particular its high spectral brightness and purity, facilitate optical density measurements of very optically dense samples. U.S. Pat. No. 4,068,956 to Taboada discloses a densitometer system which uses a pulsed dye laser for measuring highly dense samples. This system, however, is optically complex, requiring multiple components including eight lenses, one beam splitter, two mirrors, multiple filters, one wedge, one photodiode or photomultiplier and one oscilloscope. Like the double beam spectrophotometer, the Taboada system includes the light source as part of the system. As a result, it is quite costly and very large, requiring a 5 m optical bench. Undisclosed special instrumentation is required in order for the disclosed apparatus to provide adequate measurement of high energy, ultrashort pulses. The Taboada system requires independent calibration through the use of standardized filters of known optical density. In addition, the optical density filters used in this system can be subject to "bleaching" and loss of optical density properties with such ultrashort pulses. Finally, it should be noted that, to be suitable as a protector against laser radiation, a filter must maintain its optical density under exposure, not only to the high peak power densities associated with pulsed lasers, but also to the continuous wave power densities capable of eventually destroying the filter material.

The need therefore exists for a portable, simple, cost-effective densitometer which can measure optical densities to 10 and which is compatible with laser light sources of any pulse duration, continuous wave through ultrashort.

OBJECTS OF THE INVENTION

It is therefore a principal object of the present invention to provide an apparatus to measure the optical density of highly absorptive optical materials. It is a further object of the invention to provide a system capable of measuring optical density with high energy pulsed and continuous wave lasers. It is a further object of the invention to provide a compact, portable densitometer capable of performing accurate measurements in the field. It is a further object of the invention to provide a relatively simple and inexpensive system which can accurately measure optical density.

It is an advantage of the present invention that may be used to directly measure the capability of a protective filter by exposing the filter to the laser from which it is intended to provide protection.

A further advantage of the present invention is that it does not include the laser light source as part of the system; it is therefore possible to use various laser light sources.

A further advantage of the present invention is that it does not require independent calibration.

Objects and advantages of the invention are set forth in part herein and in part will be obvious herefrom, or may be attained by means of instrumentalities and combinations pointed out in the appended claims.

SUMMARY OF THE INVENTION

In accordance with the foregoing principles and objects of the invention, an apparatus for measuring optical density of highly absorptive materials is described which comprises a beam splitter, a lambertian diffusing plate, a light limiting aperture, a sample detector, a reference detector and an instrumentation amplifier. The beam splitter divides light from a laser source into a reference beam and a sample beam. The reference beam is directed to the reference detector and the sample beam is reflected off the diffusing plate and directed to a sample through the aperture. The emanations from the sample are directed to the sample detector. The instrumentation amplifier compares the intensities of the two detectors. The aperture and reference detector are positioned so that the measured intensities are equal and the optical density of the sample is calculated.

BRIEF DESCRIPTION OF THE DRAWINGS

The invention will be clearly understood from the following detailed description of preferred embodiments thereof read in conjunction with the accompanying drawing wherein FIG. 1 schematic view of the essential components of a representative densitometer of the invention.

DETAILED DESCRIPTION OF THE INVENTION

Referring now to FIG. 1, shown therein is a schematic view of the essential components of a densitometer 10 of the invention. The invention includes a beam splitter 12, a lambertian diffusing plate 14, a light limiting aperture 16, a sample detector 18, a reference detector 20 and an instrumentation amplifier 22. An incoming light beam q from a laser light source (not shown) is split by beam splitter 12 into a reference beam r and a sample beam s. Reference beam r and sample beam s are projected along respective optical axes R and S. Preferably, the light source is a high energy pulsed laser, such as a Nd:YAG/Ti:Sapphire regenerative amplifier laser system. However, it should be understood that a laser light source of any pulse duration, continuous wave through ultrashort, could be utilized to produce laser radiation at a desired wavelength. Beam splitter 12 can be selected from a set of beam splitters having different splitting ratios so that the system can be customized to give optimum results for different types of samples and detectors. For example, beam splitters such as splitter 12 are available to provide a 50%/50% splitting ratio, resulting in an equal apportionment of the energy in light beam q between split portions r and s. Alternatively, as known in the art, splitter 12 may be fabricated to provide 75% of the energy in reference beam r and 25% of the energy in sample beam s. The splitting ratio of a beam splitter such as splitter 12 is frequently defined in terms of transmission and reflection coefficients, the transmission coefficient being the ratio of transmitted to incident energies; the reflection coefficient, the ratio of reflected to incident energies. It is apparent that a beam splitter having equal transmission and reflection coefficients provides a 50%/50% splitting ratio. CVI Laser, Inc. of Albuquerque, N.Mex. can provide beam splitters with different splitting ratios for apportioning the laser energy incident thereon between the split beam potions.

Sample beam s is transmitted through a sample 24 under test to sample detector 18. Sample detector 18 thus receives transmitted beam s'. Reference beam r is reflected off lambertian diffusing plate 14 and projected along optical axis R' to reference detector 20 through light limiting aperture 16. Reference detector 20 thus receives diffusely reflected beam r'. Diffusing plate 14 and aperture 16 function to attenuate reference beam r prior to its impingement on detector 20, an important aspect of the invention as will be later explained.

In operation, detectors 18 and 20 generate output signals proportional to the intensity or power of the light incident upon them. In response to beam s', sample detector 18 produces a light signal which is indicative of the magnitude of beam s'. In response to beam r', reference detector 20 generates a signal proportional to the magnitude of beam r'. Detectors 18 and 20 can be any of the several types of detectors commercially available for this purpose. A suitable detector is a silicon detector type J3S-10 available from Molectron Detector, Inc.

Output signals from detectors 18 and 20 enter instrumentation amplifier 22, which compares these light value signals. Specifically, inside of instrumentation amplifier 22, a divisional operation dividing the output signal of sample detector 18 by the output signal of reference detector 20 is effected. A preferred embodiment is the model INA101 Instrumentation Amplifier manufactured by Burr-Brown Corporation of Tuscon, Ariz.

Important inventive aspects of densitometer 10 will now be more fully discsussed. As shown in FIG. 1, plate 14 is disposed in the path of reference beam r along optical axis R. Plate 14 is composed of polytetrafluoroethylene (PTFE) or a similar material with highly reflective characteristics. Spectralon® reflectance material, a commercially available PTFE compound available from Labsphere of North Sutton, N.H., provides a highly efficient lambertian surface. Preferably, diffusing plate 14 has a reflectance value in the range of 0.98–0.99 at the selected wavelength, the reflectance value being the ratio of reflected power to incident power. However, it should be understood that diffusing plates with differing reflectance values may be used in the invention based upon the optical density of the samples measured and the detector sensitivity. The lambertian scattering character of plate 14 reflects reference beam r with substantial uniform intensity in all directions without being affected by the bleaching of high irradences.

As shown in FIG. 1, aperture 16 is coaxial with, and positioned at a fixed distance from, detector 20. Aperture 16 narrows and focuses reflected light beam r' prior to its impingement on detector 20. It should be noted that a substantial portion of the reflected light will not enter aperture 16. However, as shown by the arrow in FIG. 1, a certain amount of reflected light will pass through aperture 16 and impinge upon reference detector 20. The reference to this light as constituting a beam of reflected light is intended to imply only that light passing in this direction. Preferably, aperture 16 is circular, the diameter d of aperture 16 being generally in the range between 0.5 and 7.0 millimeters although not limited strictly to these dimensions. However, the aperture diameter should not exceed the clear aperture diameter of reference detector 20. Preferably, the distance from aperture 16 to detector 20 is fixed at a small value in order to prevent stray light from entering detector 20. Those of ordinary skill in the art will recognize that light-blocking means can be employed to further reduce any residual effects of stray light. For example, densitometer 10 may be covered with a thin soft dark material, such as black felt, to provide protection from any ambient or scattered light generated by the laser. The detection system may also be protected from any electrical noise in the measurement environment.

As indicated previously, lambertian diffusing plate 14 and aperture 16 provide an ability to attenuate the intensity or energy of the light beam impinging on detector 20. This attenuation factor can be estimated by the following formula:

$$\frac{P_{r'}}{P_r R_r} = \frac{kS\cos\theta}{\pi x^2} \quad \text{(equation 1)}$$

Where $P_{r'}$ is the energy of beam r',
$P_r$ is the energy of beam r,
$R_r$ is the reference beam ratio correction factor for beam splitter 12,
k is the reflectance value of lambertian diffusion plate 14,
S is the area of aperture 16,
$\theta$ is the angle between optical axes R and R', and
x is the distance from diffusing plate 14 to aperture 16.

Correction factor $R_r$ is necessary to account for imperfections inherent in beam splitter 12 and is readily attainable by calibration techniques well known in the art.

Where aperture 16 is circular with diameter d, we may substitute $S=\pi d^2/4$ and solve for $P_{r'}$ as follows:

$$P_{r'} = \frac{P_r R_r k d^2 \cos\theta}{4x^2} \quad \text{(equation 2)}$$

It is apparent from equation 2 that $P_{r'}$ can be varied by varying angle $\theta$ and/or distance x and/or diameter d of aperture 16.

In operation of densitometer 10, aperture 16 and reference detector 20 are movably positioned relative to plate 14. In particular, as shown in FIG. 1, aperture 16 and reference detector 20 are positioned along axis R' at a variable angle $\theta$ relative to axis R and at a variable distance x from aperture 16 to plate 14. Aperture 16 and reference detector 20 may thus be moved, for example, by rotating axis R' in the direction of axis R thereby reducing angle $\theta$. Aperture 16 and reference detector 20 may also be moved, for example, by reducing distance x, thereby moving aperture 16 and reference detector 20 closer to plate 14. In addition, apertures having different diameters may be used in the invention. Varying angle $\theta$, distance x, and diameter d, as illustrated in these examples, will also vary the magnitude of the light signal passing to reference detector 20, as indicated in equation 2.

The operation of the above described embodiment will now be explained in detail by reference to FIG. 1. Sample 24 is placed as suggested in FIG. 1 along optical axis S. Aperture 16 and reference detector 20 are placed at arbitrarily selected positions defined by angle $\theta$ and distance x. Laser light beam q of energy P is directed toward beam splitter 12 which, in turn, projects sample beam s along optical axis S and reference beam r along optical axis R. Diffusely reflected beam r' is directed along optical axis R'. Instrumentation amplifier 22 produces a value indicative of the ratio of $P_{s'}$ (energy of beam s') to $P_{r'}$ (energy of beam r').

The positions of aperture 16 and detector 20 are changed by varying angle $\theta$, distance x, and/or diameter d until $P_{s'}=P_{r'}$, that is, until instrumentation amplifier 22 produces a ratio of 1, indicating a balanced condition. Once a balanced condition is obtained, angle $\theta$ and distance x are measured. These measured values, together with the diameter d, are used to calculate the optical density of sample 24 as fully explained below. Calibration of detectors 18 and 20 is unnecessary because the power ratio between both "arms" (that is, the sample arm and reference arm) of densitometer 10 is known when balanced, and detectors 18 and 20 may be switched to assure no differences in their response. The invention is therefore self-calibrating.

The optical density OD of sample 24 is given by the equation:

$$OD = \log_{10}\frac{P_s R_s}{P_{s'}} \quad \text{(equation 3)}$$

Where $P_s$ is the energy of beam s,
$R_s$ is the sample beam ratio correction factor for the beam splitter, and
$P_{s'}$ is the energy of beam s'.

Correction factor $R_s$ is necessary to account for imperfections inherent in beam splitter 12 and is readily attainable by calibration techniques well known in the art.

When a balanced condition is obtained, $P_{s'}=P_{r'}$. Substituting $P_{r'}$ for $P_{s'}$ in equation 3 results in the following:

$$OD = \log_{10}\frac{P_s R_s}{P_{r'}} \quad \text{(equation 4)}$$

Substituting equation 2 into equation 4:

$$OD = \log_{10}\frac{P_s R_s 4x^2}{P_r R_r k d^2 \cos\theta} \quad \text{(equation 5)}$$

It is known that $P_s=PC_t$ and $P_r=PC_r$ where $C_t$ is the transmission coefficient and $C_r$ is the reflection coefficient of beam splitter 12. Substituting these values in equation 5 and reducing leads to:

$$OD = \log_{10} C_t R_s 4 \frac{x^2}{C_r R_r k d^2 \cos\theta} \quad \text{(equation 6)}$$

For a beam splitter having a 50%/50% splitting ratio, $C_t$ is equal to $C_r$ and these coefficients cancel out, resulting in the following:

$$OD = \log_{10}\frac{R_s 4x^2}{R_r k d^2 \cos\theta} \quad \text{(equation 7)}$$

To accommodate use of noncircular apertures, equation 1 and 4 may be combined to provide the following:

$$OD = \log_{10}\frac{P_s R_s \pi x^2}{P_r R_r k S \cos\theta}$$

Substituting for $P_s$ and $P_r$ results in the following:

$$OD = \log_{10} \frac{C_t R_s \pi x^2}{C_r R_r k S \cos\theta} \quad \text{(equation 8)}$$

Using measured values of angle θ and distance x, together with aperture area S, equation 8 may be solved to yield the optical density of the sample. Simplified equation 6 may be used with a circular aperture 16 having diameter d. Further simplified equation 7 may be used for a beam splitter 12 having a 50%/50% splitting ratio.

It should be noted that it has been assumed that densitometer 10 is set up so that sample beam s is transmitted through beam splitter 12 while reference beam r is reflected from beam splitter 12. In this case, as noted above, $P_s$=$PC_t$ and $P_r$=$PC_r$. It is noted that it is also possible to set up densitometer 10 so that sample beam s is reflected from beam splitter 12 and reference beam r is transmitted through beam splitter 12. In this case, $P_s$=$PC_r$ and $P_r$=$PC_t$. These values may be substituted into equations 5 and 8 to solve for optical density.

The invention therefore provides a field usable novel apparatus and method for measuring optical density. It is understood that modifications to the invention may be made as might occur to one with skill in the field of the invention within the scope of the appended claims. All embodiments contemplated thereunder which achieve the objects of the invention have therefore not been shown in complete detail. Other embodiments may be developed without departing from the spirit of the invention or from the scope of the appended claims.

We claim:

1. A densitometer comprising:
   (a) a splitter for splitting a laser into a sample beam, which may pass through an optical element under test, and a reference beam;
   (b) a first photodetector disposed to receive light passing through the optical element;
   (c) a lambertian diffusing plate disposed to be in the path of the reference beam to diffusely reflect the reference beam;
   (d) reflected light detector means comprising a light limiting aperture and a second photodetector disposed in a fixed coaxial relationship therewith so that a beam of diffusely reflected light may pass through said aperture and enter said second photodetector, said reflected light detector means being movably disposed at an angle θ relative to the path of the reference beam and at a distance x from said diffusing plate to said aperture, so that angle θ and distance x may be varied thereby varying the intensity of light which may be received by said second photodetector; and,
   (e) an instrument amplifier for comparing light intensity values received by said first and second photodetectors whereby, when the light values are equal, angle θ and distance x have the following relationship to the optical density of the optical element:

$$OD = \log_{10} \frac{P_s R_s \pi x^2}{P_r R_r k S \cos\theta}$$

where OD is the optical density of the optical element,
$P_s$ is the intensity of the sample beam,
$R_s$ is the sample beam ratio correction factor for said splitter,
$P_r$ is the intensity of the reference beam,
$R_r$ is the reference beam correction factor for said splitter,
k is the reflectance value of said lambertian diffusing plate, and
S is the aperture area of said limiting aperture.

2. A densitometer as set forth in claim 1 wherein the sample beam is transmitted through said splitter and the reference beam is reflected from said splitter, whereby, when the light values are equal, angle θ and distance x have the following additional relationship to the optical density of the optical element:

$$OD = \log_{10} \frac{C_t R_s \pi x^2}{C_r R_r k S \cos\theta}$$

where $C_t$ is the reflection coefficient of said splitter, and
$C_r$ is the transmission coefficient of said splitter.

3. A densitometer as set forth in claim 1 wherein said light limiting aperture has a circular aperture, whereby, when the light values are equal, angle θ and distance x have the following additional relationship to the optical density of the optical element:

$$OD = \log_{10} \frac{P_s R_s 4x^2}{P_r R_r k d^2 \cos\theta}$$

where d is the diameter of the aperture of said limiting aperture.

4. A densitometer as set forth in claim 1 wherein said lambertian diffusing plate is composed of polytetrafluoroethylene compound.

5. A densitometer as set forth in claim 1 further comprising light shroud means for reducing the amount of ambient light entering said first and second photodetectors.

* * * * *